United States Patent
Chen et al.

(10) Patent No.: US 8,759,289 B2
(45) Date of Patent: Jun. 24, 2014

(54) METHOD FOR SENSITIZING CANCER STEM CELLS TO CANCER THERAPY

(75) Inventors: Wen Yuan Chen, Greer, SC (US); Eric H. Lee, Greenville, SC (US)

(73) Assignee: Orbis Health Solutions LLC, Greenville, SC (US)

( * ) Notice: Subject to any disclaimer, the term of this patent is extended or adjusted under 35 U.S.C. 154(b) by 0 days.

(21) Appl. No.: 13/576,737

(22) PCT Filed: Feb. 2, 2011

(86) PCT No.: PCT/US2011/023426
§ 371 (c)(1),
(2), (4) Date: Oct. 15, 2012

(87) PCT Pub. No.: WO2011/097268
PCT Pub. Date: Aug. 11, 2011

(65) Prior Publication Data
US 2013/0040876 A1 Feb. 14, 2013

Related U.S. Application Data

(60) Provisional application No. 61/301,062, filed on Feb. 3, 2010.

(51) Int. Cl.
*A61K 38/22* (2006.01)
*A61P 39/00* (2006.01)

(52) U.S. Cl.
USPC ....... 514/11.5; 424/277.1; 530/399; 514/19.5

(58) Field of Classification Search
None
See application file for complete search history.

(56) References Cited

U.S. PATENT DOCUMENTS

| | | | | |
|---|---|---|---|---|
| 5,534,617 | A | * | 7/1996 | Cunningham et al. ........ 530/399 |
| 5,681,809 | A | * | 10/1997 | Kopchick et al. ............ 514/11.3 |
| 6,238,644 | B1 | * | 5/2001 | Rillema ...................... 424/1.61 |
| 7,115,556 | B2 | * | 10/2006 | Chen et al. .................. 514/11.5 |
| 2001/0049350 | A1 | | 12/2001 | Cincotta et al. |
| 2004/0142852 | A1 | | 7/2004 | Younis et al. |
| 2008/0038369 | A1 | | 2/2008 | Clark |
| 2008/0096795 | A1 | | 4/2008 | Weiner et al. |
| 2009/0317855 | A1 | | 12/2009 | Lengyel et al. |

FOREIGN PATENT DOCUMENTS

| | | |
|---|---|---|
| JP | 10-182699 A | 7/1998 |
| WO | WO 2006/010891 A2 | 2/2006 |
| WO | WO 2007/047803 A2 | 4/2007 |
| WO | WO 2008/074865 A1 | 6/2008 |
| WO | WO 2009/013621 A3 | 1/2009 |

OTHER PUBLICATIONS

Altschul et al,. "Gapped BLAST and PSI-BLAST: a new generation of protein database search programs," Nucleic Acids Research, 1997, 25(17):3389-3402.
Altschul et al., "Basic Local Alignment Search Tool," J. Mol. Biol., 1990, 215:403-410.
Chen et al., "A Human Prolactin Antagonist, hPRL-G129R, Inhibits Breast Cancer Cell Proliferation through Induction of Apoptosis," Clinical Cancer Research, Nov. 1999, 5:3583-3593.
Gish et al., "Identification of protein coding regions by database similarity search," Nature Genetics, Mar. 1993, 3:266-272.
Madden et al., "Applications of Network BLAST Server," Meth. Enzymol., 1996, 266:131-141.
Reynolds et al,. "Expression of Prolactin and Its Receptor in Human Breast Carcinoma," Endocrinilogy, 1997, 138(12):5555-5560.
Tourane et al,. "Increased expression of prolactin receptor gene assessed by quantitative polymerase chain reaction in human breast tumors versus normal breast tissues," J. Clin. Endocrinol. Metab., Feb. 1998, 83(2):667-675, Abstract only.
Zhang et al., "PowerBLAST: A New Network BLAST Application for Interactive or Automated Sequence Analysis and Annotation," Genome Research, 1997, 7:649-656.
Bhatavdekar et al,. "The Clinical Significance of Prolactin, TPS, CA 15-3 and CEA in Patients with Breast Cancer," Breast Disease, Jan. 1, 1993, 6:177-183.
Bonneterre et al., "Prolactin (PRL) and Breast Cancer," European Journal of Cancer and Clinical Oncology, Feb. 1, 1990, 26(2):154.
Clevenger et al., "The Role of Prolactin in Mammary Carcinoma," Endocrine Reviews, Feb. 1, 2003, 24(1):1-27.
Langenheim et al., "Two Wrongs Can Make a Right: Dimers of Prolactin and Growth Hormone Receptor Antagonists Behave as Agonists," Molecular Endocrinology, Jan. 1, 2006, 20(3):661-674.

* cited by examiner

*Primary Examiner* — Elly-Gerald Stoica
(74) *Attorney, Agent, or Firm* — Foley & Lardner LLP (57) ABSTRACT

Disclosed herein are compositions and methods useful for the treatment of cancer, such as breast cancer. In some embodiments, the methods and compositions include human prolactin, or human prolactin in conjunction with a cytotoxic agent. In other embodiments, the methods and compositions include one or more of human prolactin, growth hormone and placental lactogen, or one or more of human prolactin, growth hormone and placental lactogen in conjunction with a cytotoxic agent. In some embodiments, the cytotoxic agent comprises a chemotherapeutic agent.

9 Claims, 4 Drawing Sheets

Control

Dox (25ng/ml)

hPRL (0.5ug/ml)

hPRL + Dox

FIG. 4B control

Dox (25ng/ml)

hPRL (0.5ug/ml)

hPRL + Dox

METHOD FOR SENSITIZING CANCER STEM CELLS TO CANCER THERAPY

CROSS-REFERENCE TO RELATED PATENT APPLICATION

This application is the U.S. National Stage of PCT/US2011/023426, filed Feb. 2, 2011, which claims priority from U.S. Provisional Application No. 61/301,062, filed Feb. 3, 2010, incorporated herein by reference in its entirety.

BACKGROUND

Breast cancer is the most common malignancy among women and has one of the highest fatality rates of all cancers affecting females. Breast cancer remains the leading cause of cancer deaths in women aged 20-59.

It is well established that prolactin and growth hormone play a role in the development and progression of breast cancer. For example, higher serum level of lactogenic hormones have been found in some breast cancer patients, and 40-70% of breast cancer biopsies were positive for the presence of the prolactin receptor. Indeed, most human breast cancer cells in culture contain prolactin receptors, and the majority of breast cancer cell lines overexpress the prolactin receptor 2-10 fold. For example, T47D and MCF-7 both contain high levels of prolactin receptor and are often used as a model demonstrating the relationship between lactogenic hormones and breast cancer. Accordingly, numerous approaches to breast cancer therapy are directed to prolactin antagonists, and methods of blocking the prolactin receptor.

Similarly, a high serum level of growth hormone was found to induce the formation of breast cancer, while reduction of the circulating level of growth hormone correlated with the regression of breast cancer.

The cancer stem cell (CSC) theory states that tumors are organized in a cellular hierarchy, in which CSCs are the only cells with unlimited proliferation potential and the capability of driving tumor growth and progression. Therefore, efforts are also being made to develop cancer therapeutics which target cancer stem cells. However, recent studies show that the use of conventional chemotherapy in neoadjuvant regimens could actually lead to enrichment in CSCs, suggesting that CSCs may be generally resistant to chemotherapy. Indeed, the lack of responsiveness of CSCs to chemotherapy explains why clinically, tumor size is often initially reduced in response to chemotherapeutic drugs but then relapses.

Several lines of evidence have strongly linked PRL to breast cancer development, and expression levels of prolactin receptors (PRLR) reportedly are higher in human breast cancer cells than in normal breast epithelial cells (Reynolds et al., *Endocrinology*, 138:5555-60 (1997)) or in surgically removed breast cancer tissues (Touraine, Martini P. et al., *Increased Expression Of Prolactin Receptor Gene In Human Breast Tumors Versus Contiguous Normal Breast Tissues*, (Abstract) 79th Annual Meeting of Endocrine Society, p. 113, (1997)). Prolactin has also been shown to act as an anti-apoptotic agent and anti-prolactin agents have been shown to induce apoptosis in breast cancer cells (Chen et al., *Clin. Cancer Res.* 5:3583-93 (1999)). The present invention, however, discloses the unexpected discovery that prolactin can be used in a method for treating breast cancer.

SUMMARY OF THE INVENTION

Disclosed herein are compositions and methods useful for the treatment of cancer, such as breast cancer. The compositions and methods of the present invention comprise pretreating cancer cells with a lactogenic hormone, and simultaneously or sequentially administering a cytotoxic agent, such as a chemotherapeutic agent. In one embodiment, the lactogenic hormone is human prolactin, growth hormone, or placental lactogen. In another embodiment, one or more of human prolactin, growth hormone and placental lactogen, is/are administered simultaneously or sequentially with a cytotoxic agent, such as a chemotherapeutic agent.

For example, described herein is a method of reducing the number of cancer cells in a patient comprising administering a therapeutically effective amount of a lactogenic hormone to a patient and concurrently or sequentially administering a therapeutically effective amount of a cytotoxic agent. In one embodiment, the lactogenic hormone is selected from the group consisting of prolactin, growth hormone, placental lactogen and a combination thereof.

Also described is method for treating a patient having cancer or reducing the risk of recurrence of a cancer in a patient diagnosed with the cancer, comprising administering lactogenic hormone to a patient and concurrently or sequentially administering a therapeutically effective amount of a cytotoxic agent. Similarly, described herein is a method of increasing the time to relapse of a cancer in a patient diagnosed with the cancer, comprising administering to the patient a therapeutically effective amount of a lactogenic hormone.

In this invention, prolactin is not being used to simply reduce the risk of occurrence of breast cancer in a patient that has not been diagnosed with breast cancer, but to treat a patient that has already been diagnosed with breast cancer. The invention also describes methods for reducing recurrence of a cancer in a patient that has already been diagnosed with cancer.

BRIEF DESCRIPTION OF THE DRAWINGS

FIG. 3A-D depicts microscopic examination of tumorsphere formation in a human MCF-7 breast cancer cell after 11 days of treatment with doxorubicin (Dox, 25 ng/ml) (FIG. 3B), human prolactin (hPRL, 0.5 μg/ml) (FIG. 3C), or in combination treatment (hPRL+Dox) (FIG. 3D). FIG. 3A shows MCF-7 control cells. The combination treatment reduced total tumorsphere number and size (arrow, FIG. 3D).

FIG. 4 depicts microscopic examination of MMTV-neu tumorsphere formation in a breast cancer cell after 11 days of treatment with doxorubicin (Dox, 25 ng/ml) (FIG. 4B), human prolactin (hPRL, 0.5 μg/ml) (FIG. 4C), or in combination treatment (hPRL+Dox) (FIG. 4D). FIG. 4A shows control cells. The combination treatment reduced total tumorsphere number and size.

DETAILED DESCRIPTION OF THE INVENTION

Disclosed herein are methods and compositions useful for the treatment of cancer, such as breast cancer. In some embodiments, the methods and compositions include a lactogenic hormone such as prolactin. While prolactin is known to play a role in the development and progression of breast cancer, the surprising and unexpected results disclosed herein demonstrate that prolactin treatment, in conjunction with conventional chemotherapeutic agents, decreases the number of both breast cancer stem cells and differentiated breast cancer cells. Without being bound by theory, it is hypothesized that the lactogenic hormone sensitizes a cancer stem cell to chemotherapeutic agents by allowing these cells to differentiate. Once the cells are in an active (non-dormant) state, they are more susceptible to treatment with a chemotherapeutic agent.

As used herein, the terms "subject" and "patient" are used interchangeably and refer to a mammal, preferably a human.

As used herein, the terms "therapeutically effective dose" or "therapeutically effective amount" means a dose that produces the desired effect for which it is administered. The exact dose will be ascertainable by one skilled in the art using known techniques, and efficacy can be measured in conventional ways. For cancer therapy, efficacy can, for example, be measured by assessing the time to disease progression, determining response rates, time to relapse, tumor size, etc.

The terms "treating", "treatment", and the like are used herein to refer to obtaining a desired therapeutic effect. The effect is therapeutic in terms of a partial or complete cure of a disease, condition, symptom or adverse effect attributed to the disease. The term "treatment", as used herein, covers any treatment of a disease in a mammal, particularly a human, and includes: (a) preventing the disease from recurring in a subject who has been diagnosed as having it; (b) inhibiting the disease, i.e., arresting or reducing the progression of the disease or its clinical symptoms in a patient diagnosed as having the disease; or (c) relieving the disease, i.e., causing regression of the disease and/or its symptoms or conditions in a patient diagnoses as having the disease. The compositions and methods disclosed herein can be used for treatment and/or for the prevention of cancer relapse or cancer reoccurrence. Thus, in some embodiments, treating cancer (e.g., breast cancer) would include decreasing the clinical indications associated with the cancer, for example decreasing tumor size, decreasing the number of cancer stem cells, decreasing the number of differentiated cancer cells, and/or increasing time to relapse or recurrence of a treated cancer or tumor.

The term "cytotoxic agent" as used herein refers to a substance that inhibits or prevents the function of cells and/or causes destruction of cells. The term is intended to include radioactive isotopes (e.g. $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include alkylating agents such as thiotepa and cyclosphosphamide (CYTOXAN)™; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, meiphalan, novembichin, phenesterine, prednimustine, trofosfamide, uracil mustard; nitrosureas such as carmustine, chiorozotocin, fotemustine, lomustine, nimustine, ranimustine; antibiotics such as aclacinomycins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, porfiromycins, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracri ne; pentostatin; phenamet; pirarubicin; podophyllinic acid; 2-ethylhydrazide; procarbazine; PSK™; razoxane; sizofiran; spirogermanium; tenuazonic acid; triaziquone; 2,2'2,"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TOXOTERE™; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (FARESTON™); and anti-androgens such as flutamide, nilutamide, bicalutamide, leuprolide, and goserelin; and pharmaceutically acceptable salts, acids or derivatives of any of the above.

In some embodiments, one or more breast cancer chemotherapeutic agents are used and include, but are not limited to the following: anthracyclines, such as doxorubicin (Adriamycin/Rubex), epirubicin (Ellence), and liposomal doxorubicin (Doxil); taxanes such as docetaxel (Taxotere), paclitaxel (Taxol), and protein-bound paclitaxel (Abraxane); cyclophosphamide (Cytoxan); capecitabine (Xeloda) and 5 fluorouracil (5 FU); vinorelbine (Navelbine); gemcitabine (Gemzar); trastuzumab (Herceptin).

The term "pharmaceutically acceptable" as used herein means approved by a regulatory agency of the Federal or a state government or listed in the U.S. Pharmacopeia or other generally recognized pharmacopeia for use in animals, and more particularly, in humans.

Pharmaceutical Compositions

The pharmaceutical compositions useful in the practice of the methods disclosed in the present invention include a therapeutically effective amount of an active agent, and a pharmaceutically acceptable carrier.

As used herein, the term "active agent" refers to a component of a composition, such as a pharmaceutical composition, that has a pharmaceutical effect on a patient. In some embodiments described herein, active agents include polypeptides such as prolactin, growth hormone, placental lactogen and fragments or variants thereof, which are capable of binding to the prolactin receptor.

According to the present invention, a cancer patients is pre-treated with prolactin, growth hormone, placental lactogen, or a combination thereof, and either concurrently treated with a chemotherapeutic agent or pre-treated with the lactogenic hormone(s) prior to administering the chemotherapeutic agent.

The prolactin for use in the present invention includes wild-type prolactin as well as conservative variants thereof. The overall structure and composition of the prolactin is important only insofar it confers the appropriate functional characteristics, i.e., prolactin receptor binding. A skilled artisan would understand that typically the prolactin for use as described herein should be species matched with the mammal being treated. For example, a human being treated with prolactin should typically be treated with a human prolactin.

A prolactin variant according to the present invention generally conserves the overall molecular structure of the protein. Given the properties of the individual amino acids in prolactin, some rational substitutions will be apparent. Amino acid substitutions, i.e. "conservative substitutions", may be made, for instance, on the basis of similarity in polarity, charge, solubility, hydrophobicity, hydrophilicity, and/or the amphipathic nature of the residues involved. Such conservative variants of prolactin retain two functional prolactin receptor binding sites and are able to initiate the prolactin signaling cascade.

For example: (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)-(d). In addition, glycine and proline may be substituted for one another based on their ability to disrupt α-helices. Similarly, certain amino acids, such as alanine, cysteine, leucine, methionine, glutamic acid, glutamine, histidine and lysine are more commonly found in α-helices, while valine, isoleucine, phenylalanine, tyrosine, tryptophan and threonine are more commonly found in β-pleated sheets. Glycine, serine, aspartic acid, asparagine, and proline are commonly found in turns. Some preferred substitutions may be made among the following groups: (i) S and T; (ii) P and G; and (iii) A, V, L and I. Given the known genetic code, and recombinant and synthetic DNA techniques, the skilled scientist readily can construct DNAs encoding the conservative amino acid variants.

Conservative variants of the present invention specifically contemplate truncations of the presently described prolactin. Truncations may be made from the N- or C-terminus, but generally do not entail deleting more than about 30% of the native molecule. In one embodiment, less than about 20%, less than about 10%, less than about 5%, or less than about 2% of the native molecule is deleted. The term "about" with regard to percentage of protein truncated connotes +/−2%. For example, deleting about 10% of the native molecules refers to a 8%-12% truncation of the native molecule. Again, so long as the prolactin (wild-type and variant prolactin) confers the appropriate functional characteristics, i.e., prolactin receptor binding and receptor dimerization and signal transduction, then it is suitable for use in the present invention.

Variants may also, or alternatively, contain other modifications, including the deletion or addition of amino acids that have minimal influence on the functional properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His).

Other prolactin variants suitable for use in the present invention are prolactin multimers, i.e., homo and heteromultimers of prolactin (including wild-type prolactin and prolactin variants) that have at least two active receptor binding sites so as to still permit receptor dimerization and signal transduction to occur. For example, a prolactin homodimer may comprise two prolactin antagonists such as G129-hPRL. Although each monomer individually is a prolactin antagonist, the homodimer acts as a prolactin agonist. In another embodiment, the prolactin multimer is a heterodimer, which comprises a prolactin antagonist (such as G129R-hPRL) and a prolactin agonist (such as wild-type prolactin). Thus, the heterodimer would be a hPRL-hPRL-G129R heterodimer.

In general, the prolactin of the present invention, and DNA encoding the prolactin, can be defined with reference to "sequence identity." Some prolactin variants have at least about 50%, at least about 55% or at least about 60% sequence identity to a wild-type prolactin. Others have at least about 65%, at least about 70%, at least about 80%, at least about 85%, at least about 90%, at least about 95%, at least about 98% or at least about 99% sequence identity to a wild-type prolactin. The term "about" with respect to a specific percentage sequence identity connotes +/−2%. For example, the term "about 95% sequence identity" refers to a range of 93%-97% sequence identity. As used herein, two nucleic acid molecules or proteins are said to "share significant sequence identity" if the two contain regions possess greater than 85% sequence (amino acid or nucleic acid) identity.

"Sequence identity" is defined herein with reference to the Blast 2 algorithm, which is available at the NCBI (http://www.ncbi.nlm.nih.gov/BLAST), using default parameters. References pertaining to this algorithm include: those found at http://www.ncbi.nlm.nih.gov/BLAST/blast_references.html; Altschul et al., (1990) "Basic local alignment search tool." J. Mol. Biol. 215: 403-410; Gish, W. & States, D. J. (1993) "Identification of protein coding regions by database similarity search." Nature Genet. 3: 266-272; Madden et al. (1996) "Applications of network BLAST server" Meth. Enzymol. 266: 131-141; Altschul et al., (1997) "Gapped BLAST and PSI-BLAST: a new generation of protein database search programs." Nucleic Acids Res. 25: 3389-3402; and Zhang, J. & Madden, T. L. (1997) "PowerBLAST: A new network BLAST application for interactive or automated sequence analysis and annotation." Genome Res. 7: 649-656. Accordingly, the prolactin peptide sequences from different species, can be aligned using standard computer programs like BLAST to inform further variation in prolactin-derived receptor-antagonizing domains that preserve their essential function.

Cell-based assay systems can be used to compare the biological activities of a wild-type prolactin and a prolactin variant. To this end, competitive binding assays may be used to ensure that each prolactin variant binds to its normal receptor and competes with wild-type prolactin for receptor binding. Competitive binding assays are routine and known in the art.

Prolactin variant activity can also be readily assessed by phosphorylation assays (e.g., immunoprecipitation assays), which are known in the art. Cell signaling via wild-type prolactin is initiated by prolactin binding to the prolactin receptor. This binding induces dimerization of the prolactin receptor, thereby triggering a signal transduction cascade in cells comprising a prolactin bound receptor. Signal transduction in the prolactin signaling pathway involves signal transducers and activators of transcription (STAT) phosphorylation, and therefore, STAT phosphorylation assays can be used to determine whether the prolactin variant is suitable for use in the present invention.

The compositions of the invention can also include a pharmaceutically acceptable carrier. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents.

Pharmaceutical compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

In some embodiments, a pharmaceutical composition including one or more active agents (e.g., one or more of prolactin, growth hormone, placental lactogen) is formulated in accordance with routine procedures as a pharmaceutical composition adapted for intravenous, subcutaneous, nasal, or intramuscular administration to human beings. Where necessary, the pharmaceutical composition may also include a solubilizing agent. In some embodiments, a local anesthetic such as lidocaine may be used to ease pain at the site of the injection. Where the composition is to be administered by infusion, it can be dispensed with an infusion bottle containing sterile pharmaceutical grade water or saline. Where the composition is administered by injection, an ampule of sterile water for injection or saline can be provided so that the ingredients may be mixed prior to administration.

The active agents can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

In some embodiments, the pharmaceutical composition includes one or more active agents (e.g., one or more of prolactin, growth hormone, placental lactogen) and one or more cytotoxic and/or chemotherapeutic active agents.

Administration

In some embodiments, one or more of prolactin, growth hormone and placental lactogen is administered concurrently with the administration of a chemotherapeutic agent, chemotherapy regimen or other cytotoxic treatment. In other embodiments, one or more of prolactin, growth hormone and placental lactogen is administered prior to the administration of a chemotherapeutic agent, chemotherapy regimen or other cytotoxic treatment. That is, the patient is pre-treated with the lactogenic hormone prior to chemotherapy or other cytotoxic treatment.

For example, in some embodiments, a pharmaceutical composition including one or more of prolactin, growth hormone and placental lactogen is administered on or about 14 days prior to the start of chemotherapy; in other embodiments, the pharmaceutical composition is administered on or about 7 days prior, on or about 5 days prior, on or about 3 days prior, on or about 2 days prior or on or about 1 day prior to the start of a chemotherapy treatment, chemotherapy regimen or other cytotoxic treatment.

In still other embodiments, one or more doses of a pharmaceutical composition including one or more of prolactin, growth hormone and placental lactogen is administered prior to the start of chemotherapy, and/or then pharmaceutical composition is administered substantially concurrent with a chemotherapy treatment or regimen. For example, in a particular embodiment, a pharmaceutical composition comprising prolactin is administered to a patient at 7 days, 5 days and 3 days prior to the start of a chemotherapy regimen, and is also administered simultaneously with the chemotherapy regimen.

In yet other embodiments, one or more of prolactin, growth hormone and placental lactogen is administered simultaneously with a chemotherapeutic agent. This "co-treatment" approach may be for the entire course of the regimen for the chemotherapeutic agent, or only the first half or first third of the regimen for the chemotherapeutic agent.

Those of skill in the art will understand that chemotherapy or other cytotoxic regimens for cancer treatment may be administered to a patient as a single treatment, or over the course of many days, weeks or months. Commonly, chemotherapy treatments are given in a 2-4 week cycle. In adjuvant and neo-adjuvant settings, they are usually given in combinations of two or more drugs. Single agent chemotherapy treatments (one drug at a time) is also an option.

For breast cancer, chemotherapy is given either by mouth or injected into a vein daily, weekly, or every 2-4 weeks, and treatment plans, which are designed for individual patient conditions can vary greatly from patient to patient.

A pharmaceutical composition including one or more active agents (e.g., one or more of prolactin, growth hormone and placental lactogen) may be administered locally, i.e. directly into or onto the tumor, or it can be administered for absorption into the blood stream. It can also be administered intramuscularly, subcutaneously, orally or topically.

The dosage of a pharmaceutical composition including one or more active agents (e.g., prolactin, growth hormone, placental lactogen) can readily be determined by the skilled artisan on a patient-by-patient basis. Factors such as patient age, weight, sex, disease state, health status, other medical conditions, other current medications or treatments, prognosis, quality of life, mode of administration, frequency of administration, and long-term treatment plans may all play a role in dosage determination, and the skilled artisan is well versed in balancing these factors to determine a proper dosage for a specific patients. In many instances, dosage may have to be determined empirically.

In some embodiments, a pharmaceutical composition including one or more of prolactin, growth hormone and placental lactogen includes a unit dose of prolactin, growth hormone and/or placental lactogen of from about 1000 mg to about 1 μg, from about 750 mg to about 50 μg, from about 500 mg to about 100 μg, from about 250 mg to about 1 mg, or from about 100 mg to about 50 mg. In some embodiments, the pharmaceutical composition includes prolactin in a unit dose of about 1000 mg, 900 mg 800 mg, 700 mg, 600 mg, 500 mg, 400 mg, 300 mg, 200 mg, 100 mg, 50 mg, 40 mg, 30 mg, 20 mg, 10 mg, 1 mg, 100 μg, 10 μg, 1 μg, 500 ng, 400 ng, 300 ng, 200 ng, 100 ng, or about 50 ng. In some embodiments, the pharmaceutical composition includes growth hormone in a unit dose of about 1000 mg, 900 mg 800 mg, 700 mg, 600 mg, 500 mg, 400 mg, 300 mg, 200 mg, 100 mg, 50 mg, 40 mg, 30 mg, 20 mg, 10 mg, 1 mg, 100 μg, 10 μg, 1 μg, 500 ng, 400 ng, 300 ng, 200 ng, 100 ng, or about 50 ng. In some embodiments, the pharmaceutical composition includes placental lactogen in a unit dose of about 1000 mg, 900 mg 800 mg, 700 mg, 600 mg, 500 mg, 400 mg, 300 mg, 200 mg, 100 mg, 50 mg, 40 mg, 30 mg, 20 mg, 10 mg, 1 mg, 100 μg, 10 μg, 1 μg, 500 ng, 400 ng, 300 ng, 200 ng, 100 ng, or about 50 ng.

Kits

Also provided herein are kits useful for the treatment of cancer, such as breast cancer. In some embodiments, the kits include pharmaceutical compositions including one or more active agents (e.g., prolactin, growth hormone and placental lactogen). In other embodiment, the kits include pharmaceutical compositions including one or more active agents (e.g., prolactin, growth hormone and placental lactogen), and a pharmaceutical composition including one or more cytotoxic agents, such as a chemotherapeutic agent. The pharmaceutical compositions may be provided in ampules, vials, packets, capsules, pre-loaded syringes, and may be provided as in solid, semi-solid, powder or liquid form.

In some embodiments, the kits include a carrier, package or container that is compartmentalized to receive one or more containers such as vials, tubes, and the like, each of the container(s) comprising one of the pharmaceutical compositions. In embodiments, the kits typically include the container described above and one or more other containers including materials desirable from a commercial and user standpoint, including buffers, diluents, filters, needles, syringes; carrier, package, container, vial and/or tube labels listing contents and/or instructions for use, and package inserts with instructions for use.

A label can be present on the container to indicate that the composition is used for a specific therapy, and can also indicate directions for in vivo use. Directions and or other information can also be included on an insert which is included with the kit.

EXAMPLES

The following examples are intended to provide those of ordinary skill in the art with a complete disclosure and description of how to make and use the methods and compositions described herein, and are not intended to be limiting.

Example 1

Co-Treatment of Human MCF-7 and Mouse MMTV-neu Cells and with Doxorubicin and hPRL MCF-7 human breast cancer cells and primary mouse breast cancer cells isolated from MMTV-neu transgenic mice were used in this study. Tumor sphere formation assay and aldehyde dehydrogenase (ALDH) activity measured by flow cytometry were used to measure the functional response of the CSCs after 11 days of co-treatment with human prolactin (hPRL) and doxorubicin (Dox).

Methods

MCF-7 and MMTV-neu cells were cultured by standard methods known in the art. Briefly, unsorted MCF-7 cells were plated in ultra-low attachment plate (Corning Inc, Corning, N.Y.) at a density of 5000 cells/ml in serum-free Dulbecco's Modified Eagle Medium-F12 (DMEM-F12) supplemented with 0.4% bovine serum albumin (BSA), 10 ng/mL of basic fibroblast growth factor (bFGF), 20 ng/ml of epidermal growth factor (EGF), 5 μg/ml of insulin (all from Sigma-Aldrich Co., St. Louis, Mo.). Tumorspheres were allowed to form in 37° C. with 5% $CO_2$ for 10 days. Culture medium were replaced two times in the course of treatment. Similar culturing method was applied to MMTV-neu cells in the exception of MMTV-neu cells were plated at a density of 200,000 cells/ml.

Cells were treated with 0.5 μg/ml of hPRL, 25 ng/ml of doxorubicin or a combination of 0.5 μg/ml hRPL and 25 ng/ml doxorubicin. After 11 days of treatment, the cells were analyzed for tumorsphere formation and ALDH activity levels.

Tumorsphere formation was determined by spheres formed in the culture medium. Spheres number were counted manually under four random fields of the 24-well at 40× magnification.

Cancer stem cells (CSCs) exhibit aldehyde dehydrogenase (ALDH) activity, while differentiated tumor cells do not. Accordingly, to determine the number of CSCs in a tumor sample, ALDH activity levels were determined by the ALDE-FLUOR kit (StemCell Technologies, Vancouver, BC, Canada). Briefly, tumorspheres were dissociated by trypsin (Invitrogen, Carlsbad, Calif.) at 37° C. for 5 minutes and resuspended in ALDEFLUOR assay buffer containing ALDH substrate (BODIPY-aminoacetaldehyde, 1 μM per $1 \times 10^6$ cells). An aliquot of the cells were treated with 7.5 μM of diethylaminobenzaldehyde (DEAB), an inhibitor of ALDH, as the negative control. Samples were incubated in 37° C. with 5% $CO_2$ for 45 minutes and analyzed by FACS-Calibur (Becton Dickinson Co., Franklin Lakes, N.J.). The ALDH-positive gate was established using the negative control treated with DEAB.

Results

Figure 1:
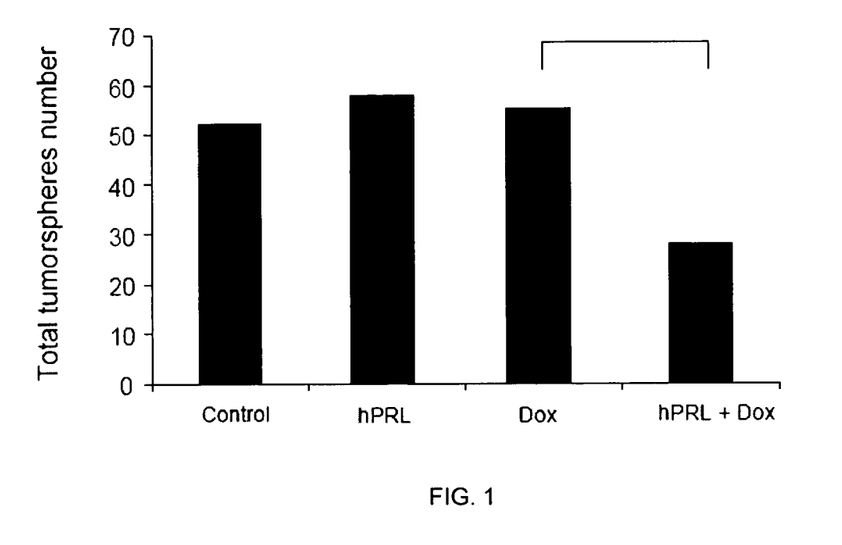
FIG. 1 is a graph showing the number of tumorspheres (size greater than 100 μm) formed in human MCF-7 breast cancer cells after 11 days of treatment with human prolactin (hPRL, 0.5 μg/ml) doxorubicin (Dox, 25 ng/ml) or in combination treatment. The combination treatment (hPRL+Dox) reduced the number of tumorspheres formed.

Results are shown in FIGS. 1-3. FIG. 1 shows the results of the tumorsphere analysis after 11 days of treatment in MCF-7 cells (data from the primary mouse breast cancer cells is not shown). As shown in FIG. 1, hPRL treatment slightly increased tumorspheres formation in MCF-7 cells. hPRL treatment also increased tumorspheres formation in primary mouse breast cancer cells (2.3-fold±0.34, p<0.001; data not shown). Dox alone had a negligible effect on tumorsheres formation; however, the combination of hPRL and Dox decreased approximately 50% of tumorspheres formation compared that of Dox treatment alone.

Figure 2:
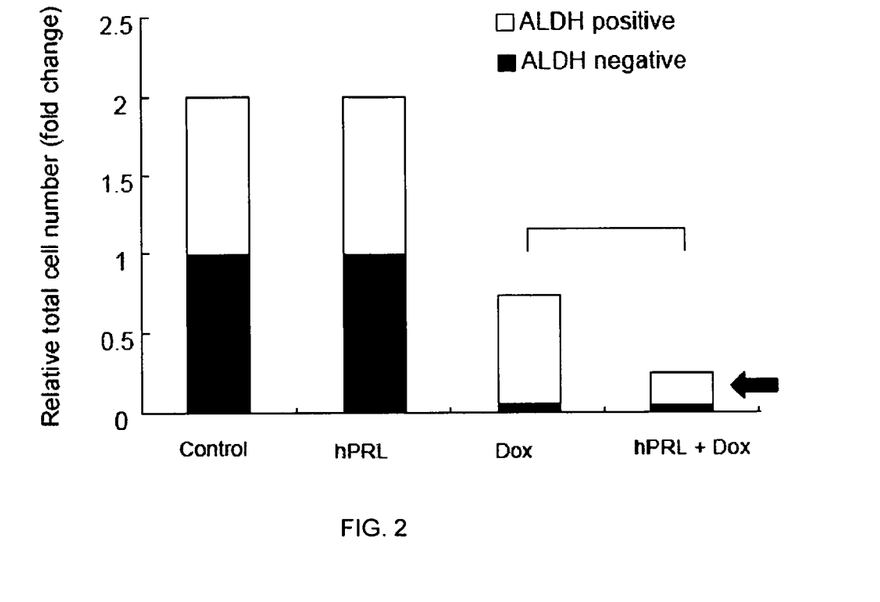
FIG. 2 is a graph showing aldehyde dehydrogenase (ALDH) expression in human MCF-7 breast cancer cells after 11 days of treatment with human prolactin (hPRL, 0.5 μg/ml) doxorubicin (Dox, 25 ng/ml) or in combination treatment. Combination treatment (hPRL+Dox) reduced the ALDH positive cell population (arrow).
Figure 3A:
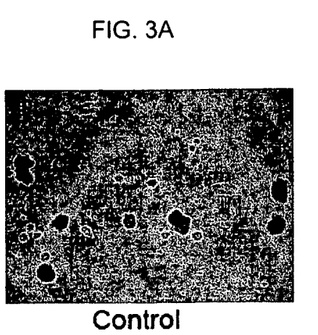
Figure 3B:
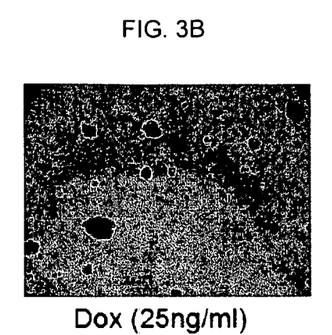
Figure 3C:
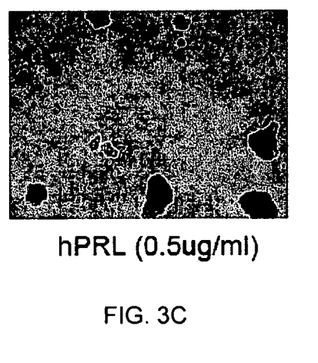
Figure 3D:
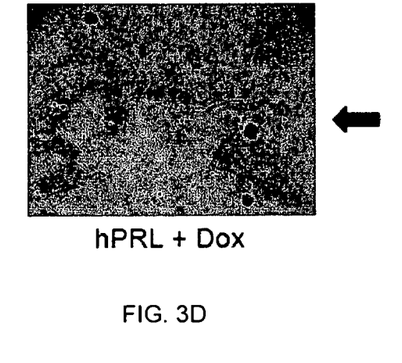
Figure 4A:
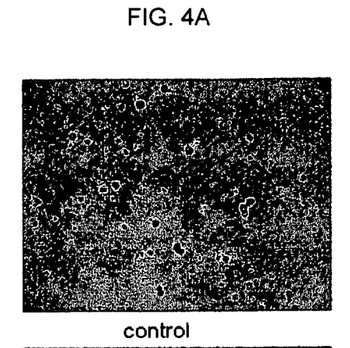
Figure 4B:
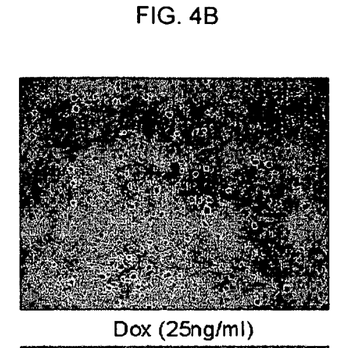
Figure 4C:
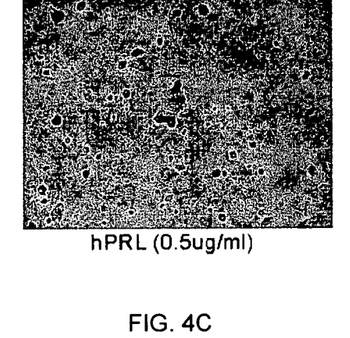
Figure 4D:
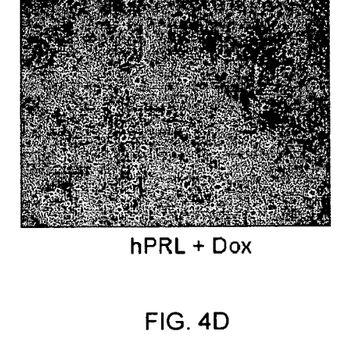

FIG. 2 shows the results of ALDH activity in MCF-7 cells tumorspheres. While Dox treatment (25 ng/ml) decreased the number of ALDH– cells, there was no significant change in total cell number of ALDH+ cell population. However, the combination of hPRL and Dox reduced the number of both ALDH+ and ALDH– cells in the tumorspheres. Accordingly, these results show that hPRL improves Dox's efficacy towards CSCs. Results with the primary mouse breast cancer cells mirrored those of the MCF-7 cells.

FIG. 3 shows a microscopic examination of MCF-7 tumorspheres after 11 days of treatment. As shown in FIG. 3D, the combination of hPRL and Dox reduced the total tumorsphere number and size (arrow). Similar results were found in MMTV-neu tumorspheres as shown in FIG. 4.

Example 2

Testing the Combination of Dox and hPRL on Additional Breast Cancer Cell Lines Methods Three breast cancer cell lines are used in this assay: two human breast cancer cell lines, MCF-7 ($ER^{high}$, $HER2^{low}$) and SKBR3 ($ER^{low}$, $HER2^{higg}$), and one mouse breast cancer cell line that was established from HER2/neu transgenic mice (McNeuA). After establishing the dose response curves, all three cell lines will be used for two in vitro studies. The cells will be treated with a standard chemotherapeutic drug, doxorubicin (Dox) alone (Max or $IC_{50}$) or in combination with hPRL (Max or $IC_{50}$).

First, the functional response of CSCs is measured by standard colony formation and tumorsphere formation assays after 7- and 14 days of treatment using methods described above in Example 2.

Next, the CSC population is measured by two sets of the stem cell markers, aldehyde dehydrogenase (ALDH) and $CD44^{high}/CD24^{low}$ after a 12-, 24- and 48 hours of treatment using flow cytometry methods as described in Example 2.

Finally, the efficacy of the treatment is examined in vivo by implanting McNeuA cell into FVB mice. Two weeks after tumor cell inoculation, a four-week treatment regimen is applied (weekly Dox with or without daily hPRL injection). Tumor growth and the time to relapse is monitored and compared among groups.

Results:

In Vitro Data:

Tumorsphere evaluation and $ALDH/CD44^{high}/CD24^{low}$ testing produces results similar to that obtained in Example 2. In other words, hPRL or Dox treatment alone has a negligible affect on tumorsphere formation in all cell lines tested, but the combination therapy (hPRL+Dox) reduces both the number and size of tumorspheres in all cell lines. The number of ALDH-negative cells is reduced with Dox treatment alone, but that ALDH-positive cell numbers are unaffected. hPRL treatment alone has a negligible affect on ALDH-positive and ALDH-negative cells, and the number of ALDH-positive and ALDH-negative cells are reduced in the combination therapy.

Expected results are summarized below in Table 1, below. With respect to the tumorsphere data, samples in which tumorspheres are comparable in size and number to the "no treatment" control group are shown as "+". Samples including tumorpheres that are smaller or fewer in number are shown as "−". With respect to the ALDH results, ALDH-positive cells are represented by the "+" or "−" on the left side of the slash, while ALDH-negative cells are represented by the "+" or "−" on the right side of the slash. ALDH results that are comparable to the no-treatment control are represented by a "+". So for example, in the Dox treated cells, the ALDH positive cell number is comparable to the "no treatment" control ("+" on the left side). In the hPRL+Dox treated samples, both ALDH-positive and ALDH-negative cell numbers are lower than the no treatment controls ("−/−").

In Vivo Data:

Tumor growth and time to relapse in the test mice (i.e., mice receiving the prolactin therapy) shows improvement when compared to the control mice, as shown in Table 2 below.

TABLE 2

In vivo results of combination therapy on McNeuA implanted mice

| | Tumor size | Time to relapse |
|---|---|---|
| No treatment | increase | no remission |
| Dox only | decrease | X days after last treatment |
| hPRL only | increase comparable to "no treatment mice" | no remission |
| Dox + hPRL | decrease comparable or greater than the "Dox only" mice | no relapse noted during the course of the study, or X + Y days after last treatment |

What is claimed is:

1. A method of reducing the number of cancer cells in a patient comprising:
   administering a therapeutically effective amount of a wild-type prolactin to a patient and concurrently or sequentially administering a therapeutically effective amount of a cytotoxic agent.

2. A method for treating a patient having cancer, comprising administering a therapeutically effective amount of a wild-type prolactin to a patient and concurrently or sequentially administering a therapeutically effective amount of a cytotoxic agent.

3. A method of reducing the risk of recurrence of a cancer in a patient diagnosed with the cancer, comprising administering a therapeutically effective amount of a wild-type prolactin to the patient and concurrently or sequentially administering a therapeutically effective amount of a cytotoxic agent.

4. The method of claim 1, wherein the cancer cells are breast cancer cells.

5. A method of increasing the time to relapse of a cancer in a patient diagnosed with the cancer, comprising:
   administering to the patient a therapeutically effective amount of a wild-type prolactin and concurrently or sequentially administering a therapeutically effective amount of a cytotoxic agent.

6. A method for treating a patient having cancer, comprising administering a therapeutically effective amount of prolactin or a variant thereof to a patient and concurrently or sequentially administering a therapeutically effective amount of a cytotoxic agent, wherein the prolactin or variant thereof is an agonist.

7. A method for treating a patient having cancer, comprising administering a therapeutically effective amount of prolactin or a variant thereof to a patient and concurrently or

TABLE 1

Tumorsphere analysis and ALDH test results

| | Tumorsphere analysis | | | | ALDH results (ALDH+/ALDH−) | | | |
|---|---|---|---|---|---|---|---|---|
| | No treatment | hPRL | Dox | hPRL + Dox | No treatment | hPRL | Dox | hPRL + Dox |
| MCF-7 | + | + | + | − | +/+ | +/+ | +/− | −/− |
| SKBR3 | + | + | + | − | +/+ | +/+ | +/− | −/− |
| MCNeuA | + | + | + | − | +/+ | +/+ | +/− | −/− | sequentially administering a therapeutically effective amount of a cytotoxic agent, wherein prolactin signal transduction is not inhibited.

8. A method of reducing the number of cancer cells in a patient comprising:
administering a therapeutically effective amount of prolactin or a variant thereof to a patient and concurrently or sequentially administering a therapeutically effective amount of a cytotoxic agent, wherein prolactin signal transduction is not inhibited.

9. The method of any of the claims 6-8, wherein the cancer is breast cancer and wherein the prolactin is wild-type prolactin.

\* \* \* \* \*